United States Patent
Henchie et al.

(10) Patent No.: US 10,603,005 B2
(45) Date of Patent: Mar. 31, 2020

(54) IMAGE-BASED METHOD TO MEASURE JOINT DEFORMITY

(71) Applicant: Worcester Polytechnic Institute, Worcester, MA (US)

(72) Inventors: Travis F. Henchie, Worcester, MA (US); Karen L. Troy, Worcester, MA (US)

(73) Assignee: Worcester Polytechnic Institute, Worchester, MA (US)

( * ) Notice: Subject to any disclaimer, the term of this patent is extended or adjusted under 35 U.S.C. 154(b) by 147 days.

(21) Appl. No.: 15/924,946

(22) Filed: Mar. 19, 2018

(65) Prior Publication Data

US 2018/0263586 A1   Sep. 20, 2018

Related U.S. Application Data

(60) Provisional application No. 62/473,404, filed on Mar. 19, 2017.

(51) Int. Cl.
| | |
|---|---|
| *A61B 5/00* | (2006.01) |
| *A61B 6/00* | (2006.01) |
| *A61B 6/03* | (2006.01) |
| *G06T 7/00* | (2017.01) |
| *G06T 19/20* | (2011.01) |
| *G06T 19/00* | (2011.01) |

(52) U.S. Cl.
CPC ............ *A61B 6/5217* (2013.01); *A61B 6/032* (2013.01); *A61B 6/505* (2013.01); *G06T 7/0014* (2013.01); *G06T 19/00* (2013.01); *G06T 19/20* (2013.01); *G06T 2207/10081* (2013.01); *G06T 2207/30008* (2013.01); *G06T 2210/41* (2013.01); *G06T 2219/2004* (2013.01); *G06T 2219/2016* (2013.01)

(58) Field of Classification Search
CPC .................................... G06T 7/00; A61B 6/00
USPC ......................................................... 382/131
See application file for complete search history.

(56) References Cited

U.S. PATENT DOCUMENTS

| | | | |
|---|---|---|---|
| 8,771,365 B2* | 7/2014 | Bojarski ............. | A61F 2/30942 623/20.32 |
| 2005/0175665 A1 | 8/2005 | Hunter et al. | |
| 2008/0107322 A1* | 5/2008 | Bi ........................ | A61B 5/4509 382/132 |
| 2011/0317898 A1 | 12/2011 | Shi et al. | |

OTHER PUBLICATIONS

PCT International Search Report in PCT/US2018/023118 dated Jun. 7, 2018.

* cited by examiner

*Primary Examiner* — Abolfazl Tabatabai
(74) *Attorney, Agent, or Firm* — Greenberg Traurig, LLP; Roman Fayerberg

(57) ABSTRACT

In some embodiments, a method for determining a deformity in a bone surface comprises performing a scan of a healthy bone and a diseased bone; creating 3-dimensional (3D) representations of a current surface of the diseased bone; constructing an estimated healthy surface in 3D for the diseased bone based on the surface of the healthy bone; and identifying a deformity in the diseased bone by comparing the estimated healthy surface to the current surface of the diseased bone. In some embodiments, the scan is performed using high resolution peripheral quantitative computed tomography (HR-pQCT).

20 Claims, 16 Drawing Sheets

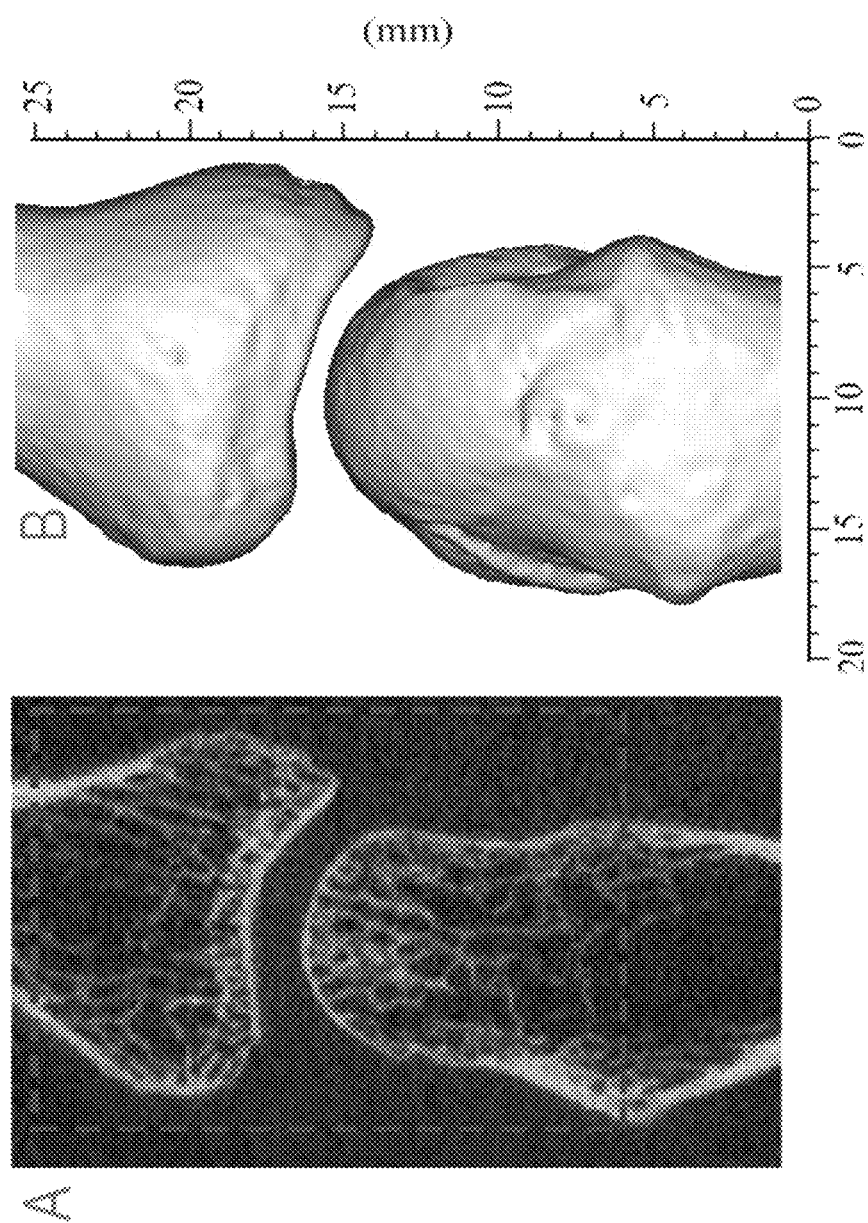

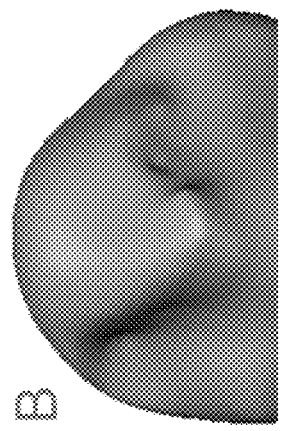
FIG. 7A
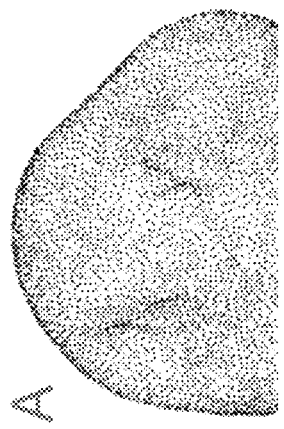
FIG. 7B
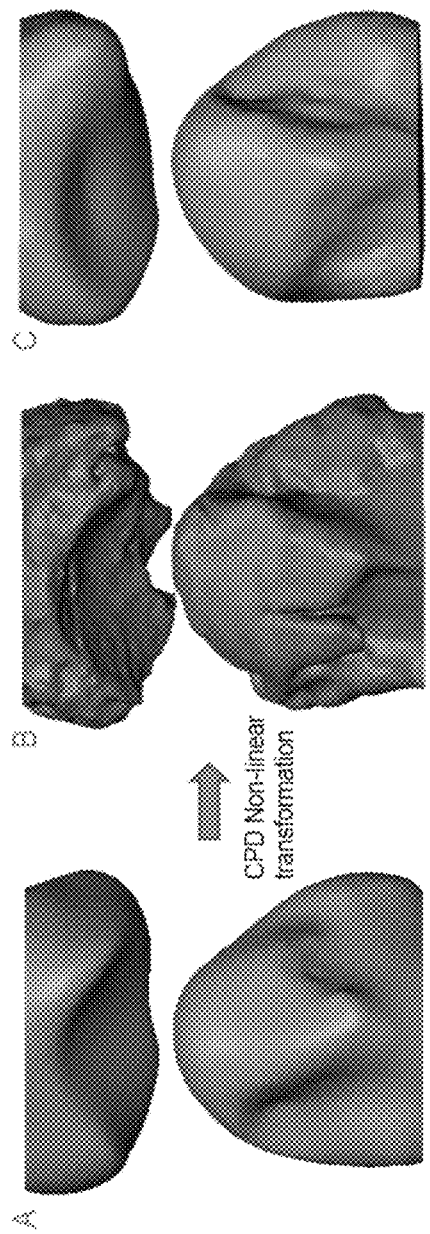
FIG. 8A
FIG. 8B
FIG. 8C

IMAGE-BASED METHOD TO MEASURE JOINT DEFORMITY

RELATED APPLICATIONS

The present application claims priority to and the benefit of U.S. Provisional Application No. 62/473,404, filed Mar. 19, 2017, which is incorporated herein by reference in its entirety.

FIELD

The present disclosure generally relates to imaging systems and methods for visualizing and quantifying joint deformity.

BACKGROUND

Psoriatic arthritis (PsA) and rheumatoid arthritis (RA) are chronic inflammatory diseases occurring in patients with autoimmune disorders and psoriasis. A combination of mechanical stress and inflammation in individuals with PsA results in the formation of periosteal bone growth (osteophytes or enthesophytes) at tendon/ligament insertion sites, and articular erosions within the joints. Erosion formation typically occurs in early disease at the proximal enthesis, but in later stages, spur formation occurs at the distal end of the ligament attachment site. The frequency and size of the abnormalities and the number of affected joints are associated with poor clinical outcomes. Some individuals exhibit extremely destructive and disfiguring forms of the disease with erosions and periosteal bone formation leading to disability. The metacarpophalangeal joints of the hand are common areas for these bone changes. Because these changes are irreversible, earlier detection and prevention may lead to improved patient care.

Accordingly, there is a need for a reliable imaging method to detect joint erosion or deformity.

SUMMARY

The present disclosure provides systems and methods for determining and identifying a deformity in a bone surface.

In some embodiments, a method for determining a deformity in a bone surface comprises performing a scan of a healthy bone and a diseased bone; creating 3-dimensional (3D) representations of a current surface of the diseased bone; constructing an estimated healthy surface in 3D for the diseased bone based on the surface of the healthy bone; and identifying a deformity in the diseased bone by comparing the estimated healthy surface to the current surface of the diseased bone. In some embodiments, the scan is performed using high resolution peripheral quantitative computed tomography (HR-pQCT).

In some embodiments, a method for determining a deformity in a bone surface comprises performing HR-pQCT scans of healthy bone surfaces in healthy cohort and of a diseased bone surface of a patient in a deceased cohort; preparing 3D images of surfaces of the healthy bone surfaces and diseased bone surface; scaling and aligning the 3D images; applying anatomical markers to the 3D images of the healthy bone surfaces; creating a 3D image of an estimated healthy surface from the 3D images of the healthy bone surfaces; non-linearly transforming the 3D image of the estimated healthy surface to the 3D image of the diseased bone surface; and displaying a comparison of the estimated healthy surface and the diseased bone surface of to identify a deformity in the diseased bone surface.

In some embodiments, a system for determining a deformity in a bone surface comprises an imaging modality; a controller in communication with the imaging modality, the controller being programmed to receive a scan of a healthy bone and a diseased bone; create 3-dimensional (3D) representations of a current surface of the diseased bone; construct an estimated healthy surface in 3D for the diseased bone based on the surface of the healthy bone; and identify a deformity in the diseased bone by comparing the estimated healthy surface to the current surface of the diseased bone; and a display for displaying the comparison between the estimated healthy surface to the current surface of the diseased bone.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 1A-1C, FIG. 2 and FIG. 3 provide flow charts of methods of the present disclosure.

FIG. 7A illustrates healthy reference vertices calculated by averaging vertices assigned to corresponding locations on the healthy cohort bone surfaces.

FIG. 7B illustrates healthy reference surface generated from the vertices of FIG. 7A.

FIG. 8A and FIG. 8B illustrates a non-linearly transformation of the reference healthy surface (FIG. 8A) into the shape of the diseased bone surface using CPD (FIG. 8B).

FIG. 8C illustrates an estimated healthy surface of the original diseased surface generated from the transformed surface from FIG. 8A.

FIG. 12B illustrates an example of a negative distance between the predicted healthy triangulated surface to the nearest diseased surface vertex in the normal direction of the respective triangle plane (erosion). FIG. 12C shows an example of a positive distance (periosteal bone formation).

Relative error=(predicted value−actual value)/actual value %.

Figures 15A, 15B:
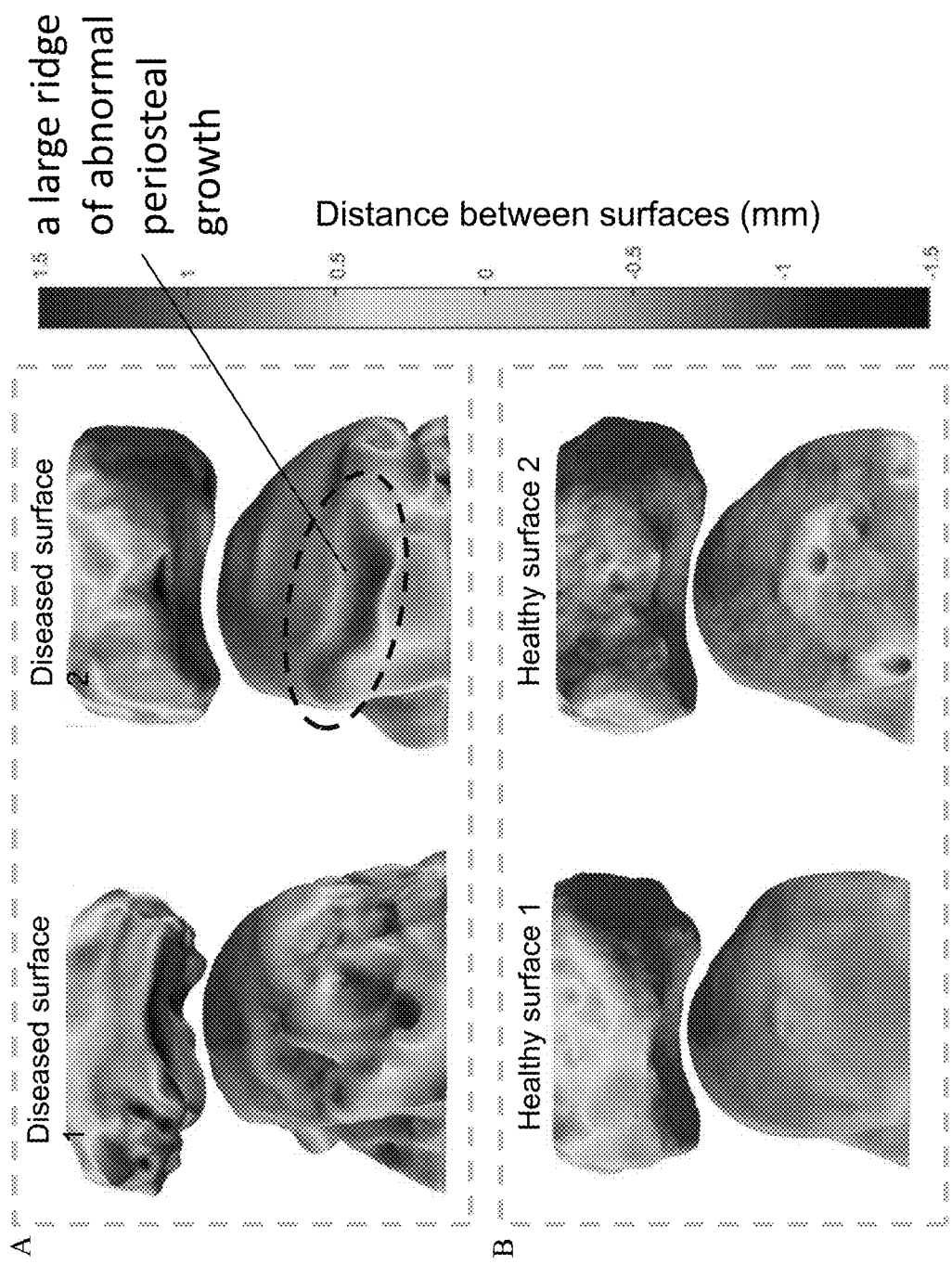

FIG. 15A and FIG. 15B illustrate the visual outputs of the algorithm showing areas of erosion and periosteal bone growth.

Figure 16:
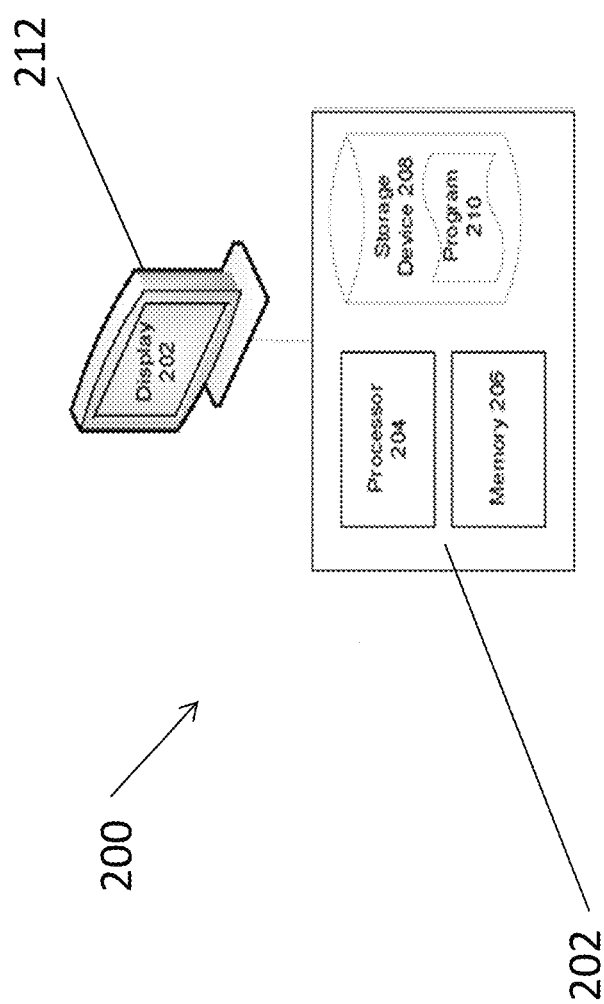

FIG. 16 is a diagram showing an exemplary computer system suitable for use with the methods and systems of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides methods and systems for quantifying joint deformity in using an imaging modality, such as, for example, ultrasound, x-ray, magnetic resonance imaging, or computed tomography. In some embodiments, the imaging modality is high resolution peripheral quantitative computed tomography (HR-pQCT). HR-PQCT is a non-invasive, low radiation method for assessing bone microarchitecture in both the trabecular and cortical regions of the distal tibia and radius, including the carpal and metacarpals of the hands, wrists, ankles and feet. It should be noted that, while HR-PQCT is used in the following discussion to describe the methods and systems of the present disclosure, other imaging modalities can also be used in connection with the methods and systems of the present disclosure. In some embodiments, the instant methods can be applied to patients with subjects with rheumatoid arthritis (RA) or psoriatic arthritis (PsA).

In some embodiments, the present systems and methods can identify bone surface abnormalities without the need of human interaction. This allows for the characterization of complex bone geometry as a result of disease destruction in a repeatable and objective manner. The instant disclosure, in some embodiments, relies on the prediction of the original healthy bone surface from the geometry of a currently diseased bone surface. Knowing the topology of the original healthy bone surface allows for the quantification of erosions with large cortical breaks and periosteal bone growths, either individually or adjacent to one another. In some embodiments, the present methods and systems can quantify bone abnormalities, by predicting where the original healthy bone surface would be.

In some embodiments, the present systems and methods are capable of estimating the position of the original healthy bone surface from the deformed bone surface, even in cases of chronic joint degradation. This may be important when quantifying erosion volume, and most of the prior art does not address this. Furthermore, the present systems and methods may be capable of identifying erosion sites and periosteal bone growths without the aid of human intervention and in cases of severe surface variation. This may become relevant when the abnormalities are not recognizable by human interpretation. In some embodiments, the present systems and methods identify individual erosions or measure individual erosion volume.

The present methods and systems are designed to objectively quantify joint deformity in rheumatoid arthritis and psoriatic arthritis affected individuals in an objective and repeatable manner. The present methods and systems can be designed to compare bone surfaces of varying sizes, express deviations in bone surface, and identify areas of periosteal bone formation and erosion sites.

The present methods and systems are capable of estimating the original healthy bone surface of a patient specific damaged bone surface using a series of three-dimensional rigid and non-rigid point set transformations. This can be carried out by acquiring HR-pQCT scans of both healthy and diseased individuals, and creating three-dimensional models from the scans. The healthy subject scans are used to develop a "generic" healthy reference bone surface, which contains inter-person variability and forms the basis of comparison to diseased or unhealthy surfaces. This healthy reference bone surface can be warped (by non-rigid transformation) to the shape of the patient specific diseased bone surfaces, whilst retaining healthy features. Variation between the transformed healthy bone surface and the original diseased bone surface can be quantified, and identified as regions of erosion or bone growth. The following outcome measures can be determined: individual erosion and periosteal bone growth locations, the singular and total volume of individual/all erosions and growths, the percentage surface areas of bone abnormalities as a function of the total bone surface, and erosion depth and growth height.

The presents methods and systems can be designed to predict a healthy surface from a patient specific three-dimensional image. They can successfully measure more erosive surface area in patients with psoriatic arthritis than healthy individuals. Erosion sites and osteophyte/enthesophyte formation is easily identifiable.

In some embodiments, the present methods and systems can be used in the clinical diagnosis of rheumatoid and psoriatic arthritis. In particular it can help quantify the extent of damage in a diseased joint surface. This method can be carried out in conjunction with existing diagnosis techniques, such as the VectraDA disease activity test. Furthermore, this method could be used to track disease progression for therapeutic intervention.

The advantages of this method may include, without limitation, increased objectivity and repeatability in quantifying joint damage by reducing reliance on human subjectivity. In some embodiments, the present systems and methods are provided with the ability to estimate a healthy bone surface using the geometry of an unhealthy bone surface. This allows for the quantification of bone surface abnormalities in chronic, heavily degraded bone surfaces and acute cases, where abnormalities are traditionally undetectable. The present methods and systems, in some embodiments, can detect bone surface changes during early onset of the disease, and detect small changes making it possible to evaluate the effects of therapy in a short time period.

In some embodiments, in reference to FIG. 1A, FIG. 1B, the instant methods may include performing HR-pQCT of healthy and diseased bones (FIG. 1A), creating 3D surfaces (FIG. 1B) of the healthy and diseased bones to construct an estimated healthy surface for diseased bones and comparing the estimated healthy surface to the current surface of the diseased bone to identify erosions and growth on the diseased bone.

Figure 1C:
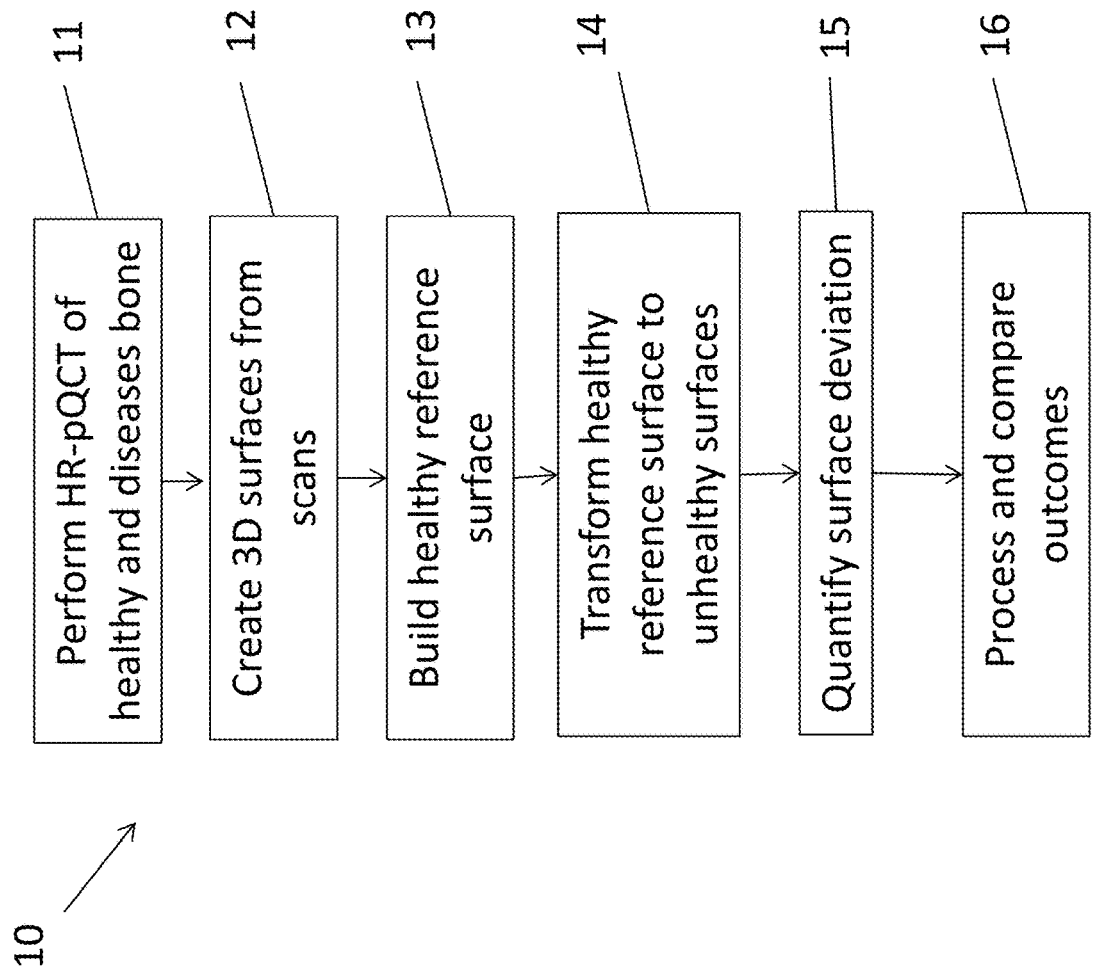

In reference to FIG. 1C, a method 10 can include the following steps: 1) Perform HR-pQCT of healthy and diseased bones in step 11; 2) Create 3D surfaces from scans in step 12; 3) Build healthy reference surface in step 13, 4) Transform healthy reference surface to diseased surfaces in step 14; 5) quantify surface deviation in step 15; and 6) Process and compare outcomes in step 16.

Figure 2:
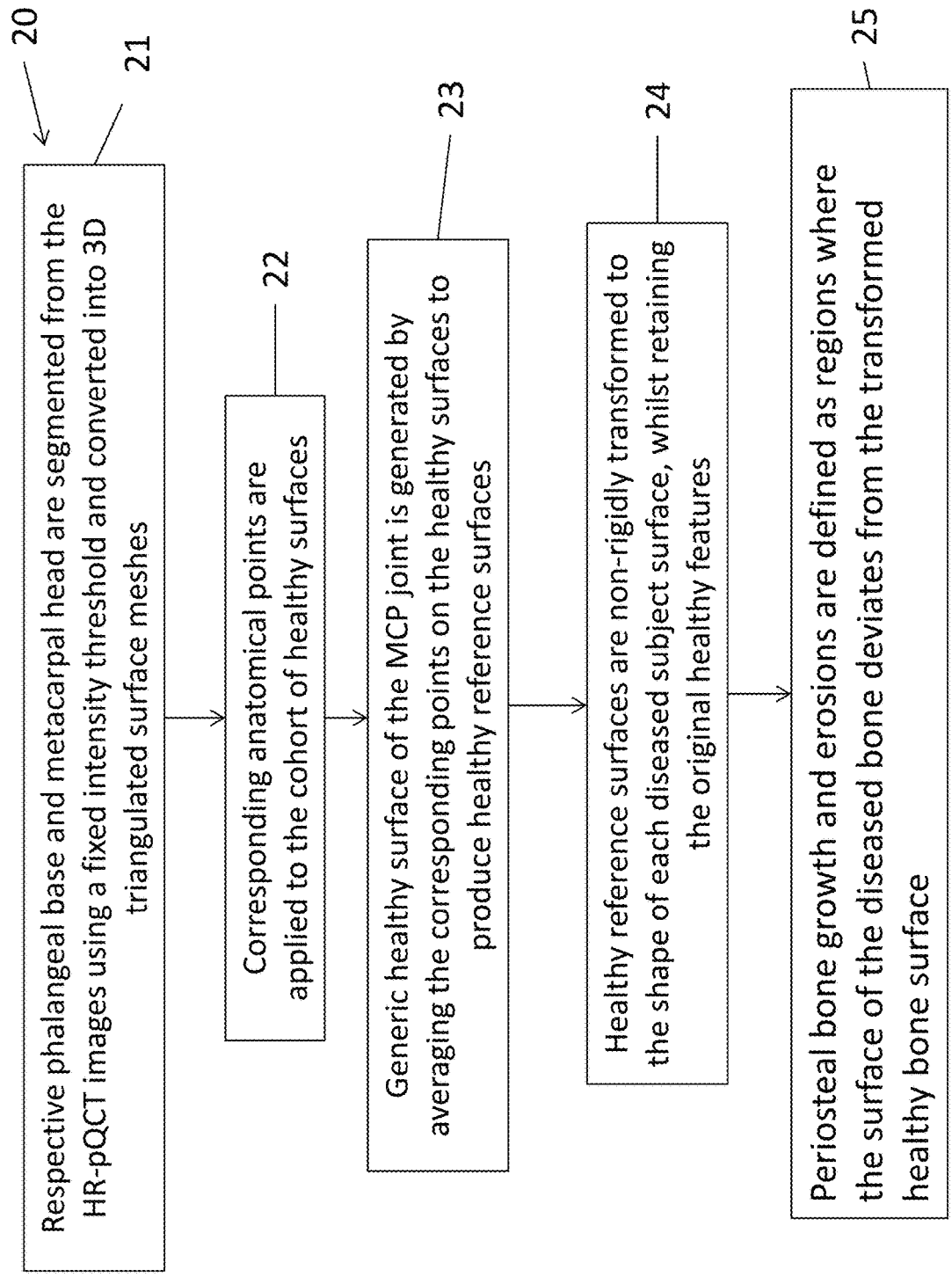

In some embodiments, in reference to FIG. 2, a method 20 can include the following steps: 1) the respective phalangeal base and metacarpal head are segmented from the HR-pQCT images using a fixed intensity threshold and converted into 3D triangulated surface meshes in step 21; (2) Corresponding anatomical points are applied to the cohort of healthy surfaces in step 22; (3) A generic healthy surface of the MCP joint is generated by averaging the corresponding points on the healthy surfaces to produce healthy reference surfaces in step 23; (4) The healthy reference surfaces are non-rigidly transformed to the shape of each diseased subject surface, whilst retaining the original healthy features in step 24; (5) periosteal bone growth and erosions are defined as regions where the surface of the diseased bone deviates from the transformed healthy bone surface in step 25.

Figure 3:
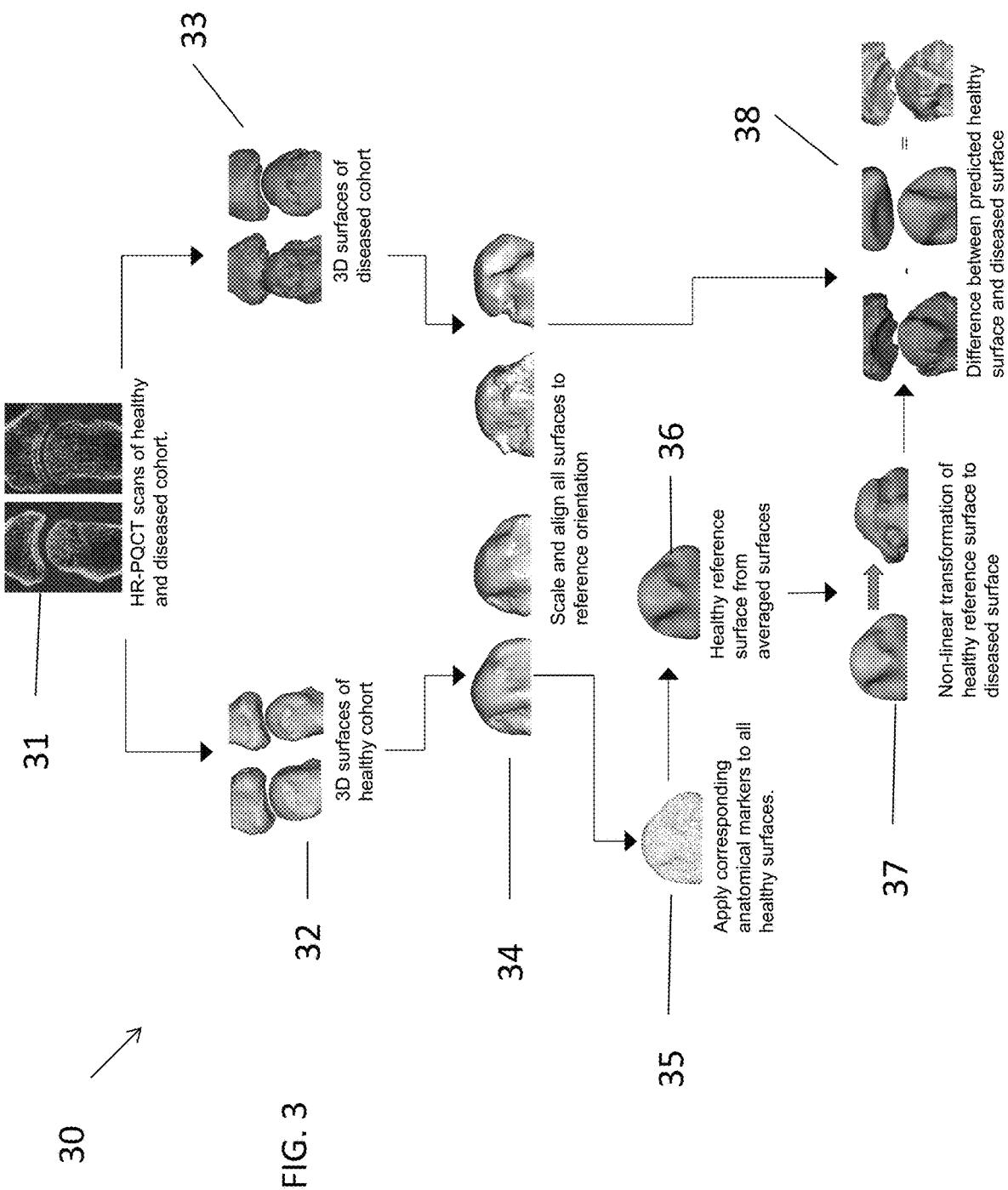

In some embodiments, in reference to FIG. 3, a method 30 can include the following steps: 1) Perform HR-pQCT of healthy bones in healthy cohort and of diseased bones for one or more patients in a deceased cohort in step 31; 2) Images of 3D surfaces of scanned bones are prepared in steps 32 and 33; 4) Images of 3D surfaces are scaled and aligned in step 34; 5) Anatomical markers are applied to all healthy surfaces in step 35; 5) Healthy reference surface is created in step 36; 6) Non-linear transformation of healthy reference surface to diseased surface is performed in step 37; and 7) Difference between predicted healthy surface and diseased surface is determined in step 38.

In some embodiments, to generate three-dimensional surfaces, HR-pQCT images can be converted to three-dimensional (3D) triangulated surface meshes (Mimics & 3Matic, Materialise NV, Leuven, Belgium, 2015) in preparation for surface-to-surface registration. The internal trabecular bone region can be excluded in this analysis, if necessary. The pixel data representing bone can be segmented using a fixed density threshold, for example 0.41 g/cm$^3$, throughout all images. A binomial blur filter can then applied to each CT slice to reduce noise, as only the outer bone surface was of interest.

Figure 4:
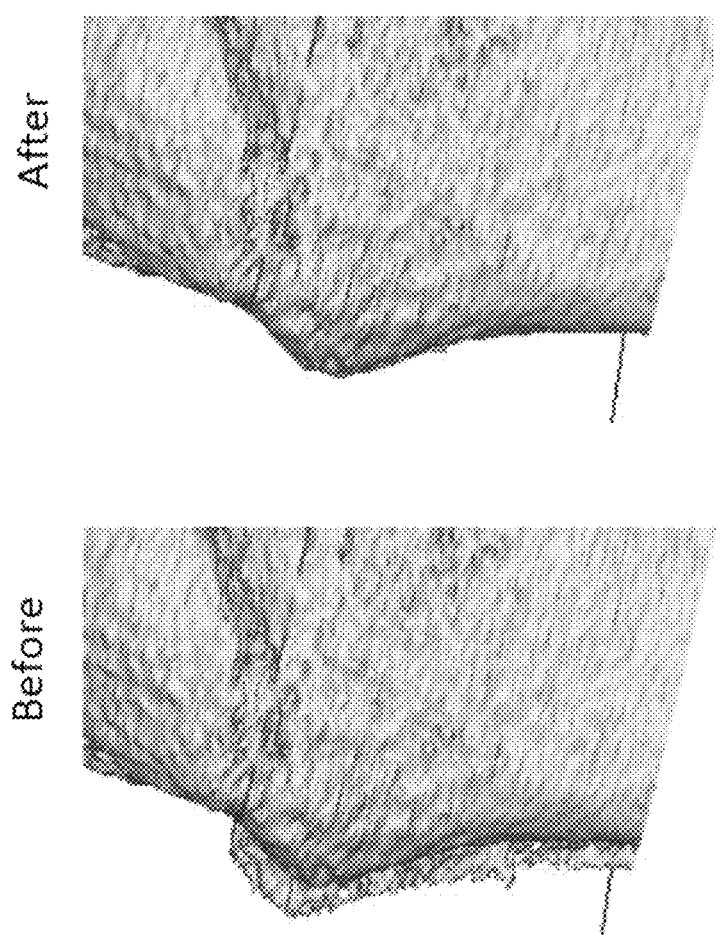
FIG. 4 illustrates before and after image of motion artifact removed in 3D.

Varied amounts of motion artifacts can be observed during the scan process and 3D surface generation. In reference to FIG. 4, a smoothing factor (for example, 0.5) can be applied during the surface generation to remove any small artefacts and irregular triangulation, as available in the Mimics 18 and 3Matic 10 software (Materialise NV, Leuven, Belgium, 2015). Such smoothing factor can be applied in multiple iterations, for example 10 or more. For larger motion induced surface irregularities, manual segmentation techniques in 3D and per slice basis (2D) can be used at the user's discretion. Furthermore, a code (MATLAB 2015a, The MathWorks, Inc., Natick, Mass., US) can be implemented during the image acquisition process to align all images between stacks. The entire imaged region of interest can be composed of multiple image stacks (for example, three image stacks (110 slices each), which can be misaligned during image construction from raw data. This misalignment would result in an inaccurate surface topology during 3D surface generation. Lastly, to reduce cortical fenestration in the segmented mask because of poor imaging quality, a surface wrap can be specified for the 3D surface with a gap closing distance of 0.2 mm. This distance can be chosen as per observations made in this study and fall below the size of fenestration in which cortical breaks are observed. For example, cortical breaks smaller than 0.2 mm can be deemed not clinically relevant and therefore, where necessary, can be excluded. Since only the bone surface is of interest, the bone cavity can be filled in to get the outer bone surface. The purpose of this step is to close any gaps in the cortical surface.

Figure 5:
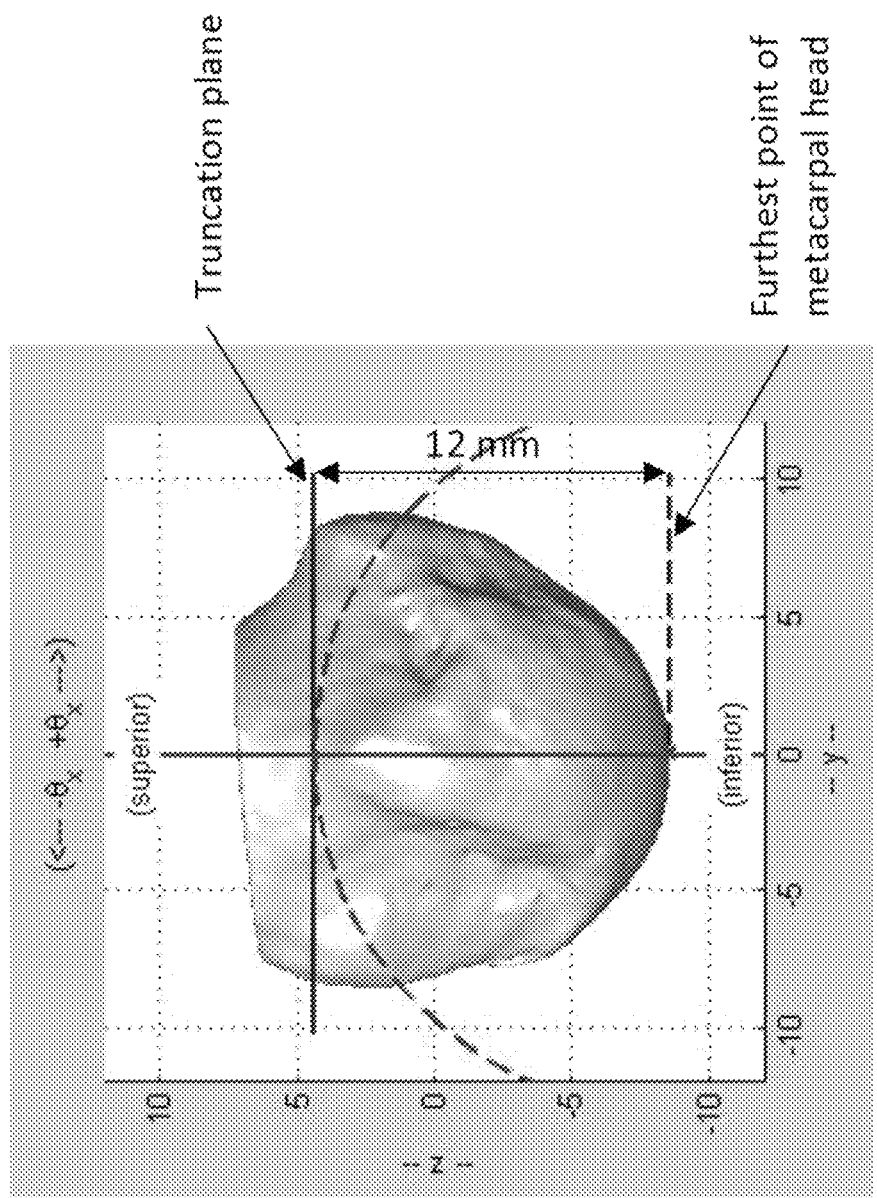
FIG. 5 illustrates a metacarpal surface showing the truncation plane relative to the metacarpal head.

In some embodiments, to scale and orient surfaces, to define a common analysis region, all surfaces can be equivalently proportioned based on bony landmarks. This can help to reduce variability between subjects of different sizes by normalizing inter-subject bone volume and spatial position. For example, to define a common analysis region, all the surfaces' (metacarpals and phalanges) centroids can be aligned and volumes scaled to a specific reference size and orientation. This can be carried out using a rigid probabilistic transformation, such as a CPD algorithm, where only translation, rotation and scaling transformations are carried out. This can include mirroring all left-hand surfaces to a right-handed orientation. The scaled and aligned healthy 3D meshes can be truncated proportionally, according to a fixed distance from the joint space as shown in FIG. 5. For example, the distance can be the distance from distal tip of metacarpal to posterior lateral tubercle. In some embodiments, the distance can be the distance or proximal lateral process tip to largest cross-sectional area. For example, the distance can be 12 mm for the metacarpal head and 9 mm for the phalangeal base. The truncation can be carried out in MATLAB 2015a (The MathWorks, Inc., Natick, Mass., US).

Figure 6:
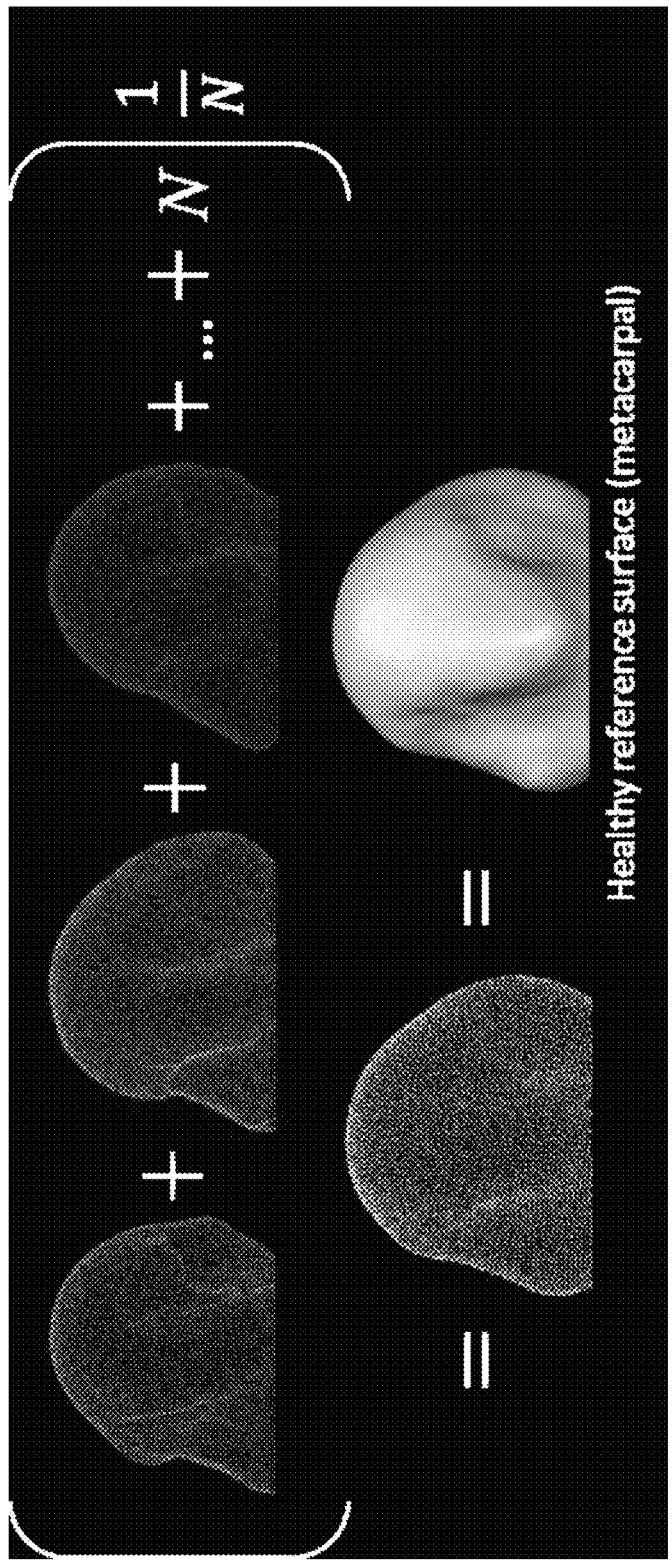
FIG. 6 is a visual representation of averaging healthy pointclouds to create generic healthy surface.

In some embodiments, to create or estimate a healthy reference surface, a composite image or a single "generic" healthy reference surface can be produced from multiple healthy subject surfaces, as shown in FIG. 6. The proportioned healthy surfaces can be characterized by vertices located at corresponding anatomical locations. In some embodiments, the proportioned healthy surfaces can be characterized by M=10,000 vertices (average vertex point-to-point resolution of 0.28 mm) positioned at corresponding anatomical locations. This can allow for a point-to-point correspondence between each n-{number of healthy surfaces} in the form of comparable point sets. This can be carried out by mapping the dense, template point set Y=(y1, . . . , yM) in $\mathbb{R}^3$ to each healthy surface point set X=(x1, . . . , xn) using a non-rigid, modified Coherent Point Drift (CPD) transformation. The CPD algorithm is a probabilistic Gaussian mixture model (GMM), non-rigid transformation technique used to register two dissimilar point sets.

In reference to FIGS. 7A and 7B, the result can be a single healthy reference surface from average pointcloud, generated by averaging the Euclidean space between all the corresponding transformed template point sets Y' to get a single average point set, such that:

$$\text{Healthy Reference Surface} = \frac{\sum_{i=1}^{n} Y'_i}{n}, \text{ where } i = 1, \ldots, n.$$

In some embodiments, to estimate healthy surfaces from diseased patient scans and to differentiate between healthy and diseased surface regions, the healthy reference surface can be non-rigidly transformed to each patient surface mesh. The result can be a new bone surface with healthy features that had similar size and geometry to the diseased surface. To accomplish this, a CPD algorithm can be adapted to warp the reference healthy surface mesh (FIG. 8A) into the shape of each patient specific diseased surface mesh (FIG. 8B), whilst retaining the "healthy" features. This allows prediction of the geometry of a patient healthy surface (FIG. 8C) from the diseased surface.

The CPD algorithm can be used to allow the user choose parameters to essentially control the rigidity of the non-linear transformation. A reference point set can be transformed to the exact shape of the target point set (less rigid) or retain more features of the reference point set (more rigid) controlled predominantly by two parameters: $\beta$ and $\lambda$. Parameter $\beta$ controls the organization and strength of interaction between points in a set. Small values of $\beta$ correspond to locally smooth transformation, vice versa large values of $\beta$ will produce pure translation transformation. Simply, parameter $\beta$ maintains the order and relation between points representing a surface to retain the shape of the reference point set. Parameter $\lambda$ represents the trade-off between data fitting and smoothness regularization, which in part controls the rigidity of the transformation and has a small role in controlling the capture size (or kernel size) of the GMM component. The capture size can be important as there may exist an ideal ratio between this and the volume/size of the surface and its features to be transformed.

Figure 9:
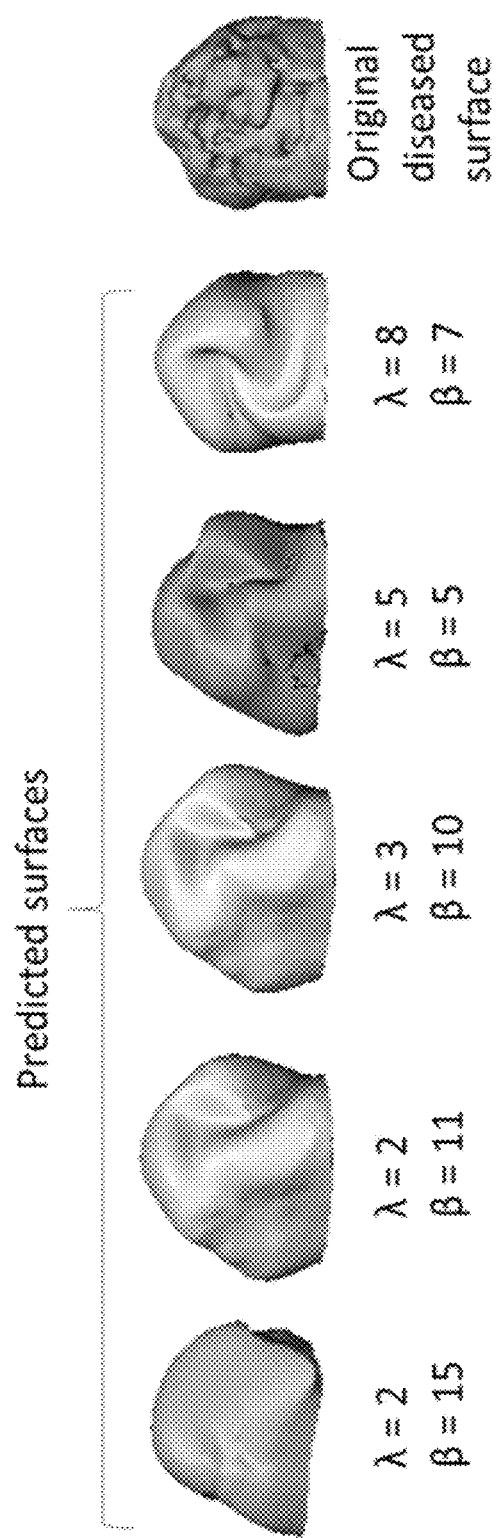
FIG. 9 illustrates predicted healthy surfaces with varying parameter values compared to the original diseased bone surface.

Initial tests can be carried out to help determine the ideal combination of parameters to suit the metacarpophalangeal joint and a typical erosion volume. For example, for a similar size, low complexity 3D object, $\beta=3$ and $\lambda=2$ can be used. This preliminary process entails transforming a healthy surface to the shape of an unhealthy surface with varying parameter values, increasing from low to high. In general, higher $\beta$ values retain more of the reference surface's healthy features, whilst lower values of $\lambda$ provide better transformation shape matching to the diseased surface. In some embodiments, an acceptable value of $\beta=11$ and $\lambda=2$ are chosen from visual confirmation, as shown in FIG. 9.

Additional parameter testing can be carried out to determine if the chosen parameters are acceptable for the proposed application in terms of predicting healthy bone surface in the presence of a typical erosion. To do this, a known volume of 26 mm$^3$ is removed from a healthy bone surface segmented in Mimics 18 software (Materialise NV, Leuven, Belgium, 2015) to represent a typical erosion. A generic reference surface is transformed to the bone surface with the manufactured erosion. The predicted volume of the erosion is measured from the difference in volume between the transformed surface (predicted healthy surface) and the bone surface with erosion. Also, the predicted healthy surface volume is compared to the original healthy bone surface (without manufactured erosion) to indicate the accuracy of the predicted healthy bone surface to a real surface. These steps are repeated for increasing values of $\beta$ in increments of two starting at 1 through to 11. An acceptable $\beta$ is chosen when the CPD code ignores the erosion and predicts the original healthy surface at the erosion region of interest. Thereafter, multiple simulations are run by varying the parameter $\lambda$ from 1 to 9. The ideal combination of $\beta$ and $\lambda$ predicts a healthy surface at the erosion site and transforms to the shape of the original bone surface (no erosion). The parameters have successful outcomes when the measured erosion volume tends to zero and the total predicted bone volume tends to the original healthy bone volume.

Figure 10:
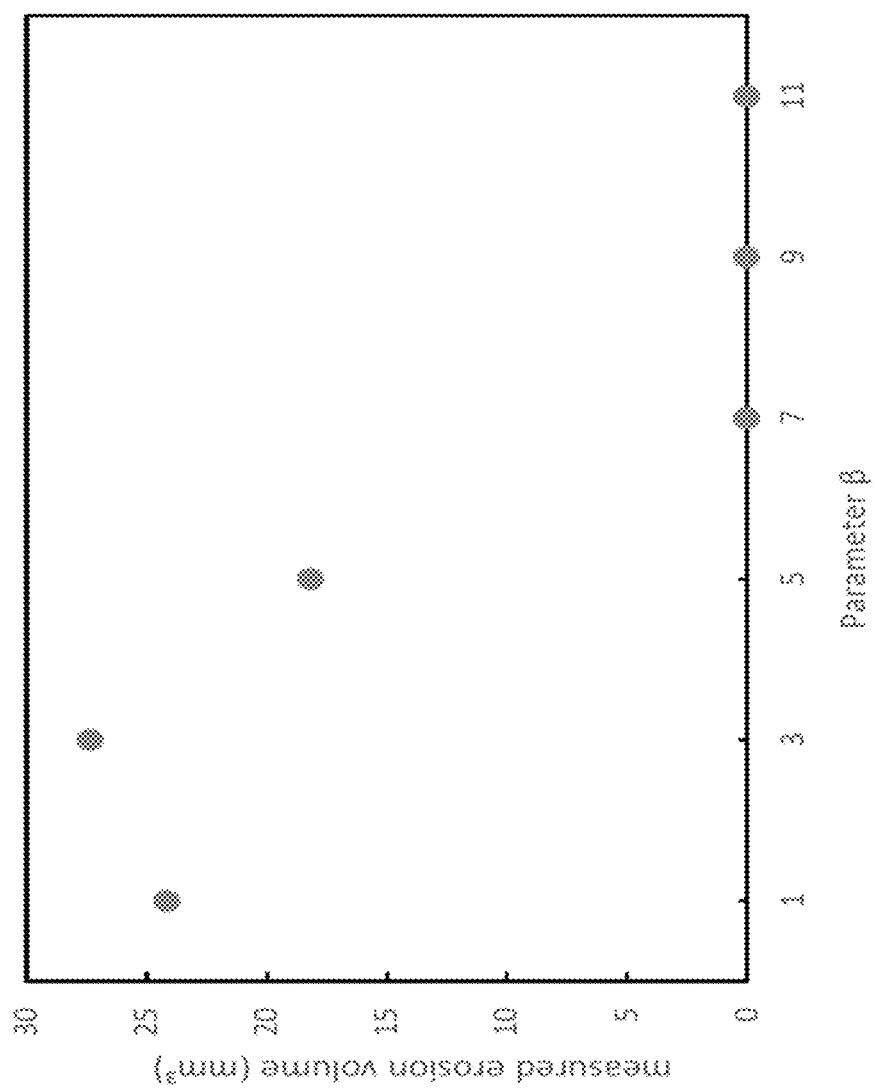
FIG. 10 illustrates the effects of parameter β on the measured erosion volume. Ideally, the parameter should cause the transformation to not be affected by the erosion and accurately predict the healthy surface. Therefore, an erosion volume of 0 is desirable.
Figure 11:
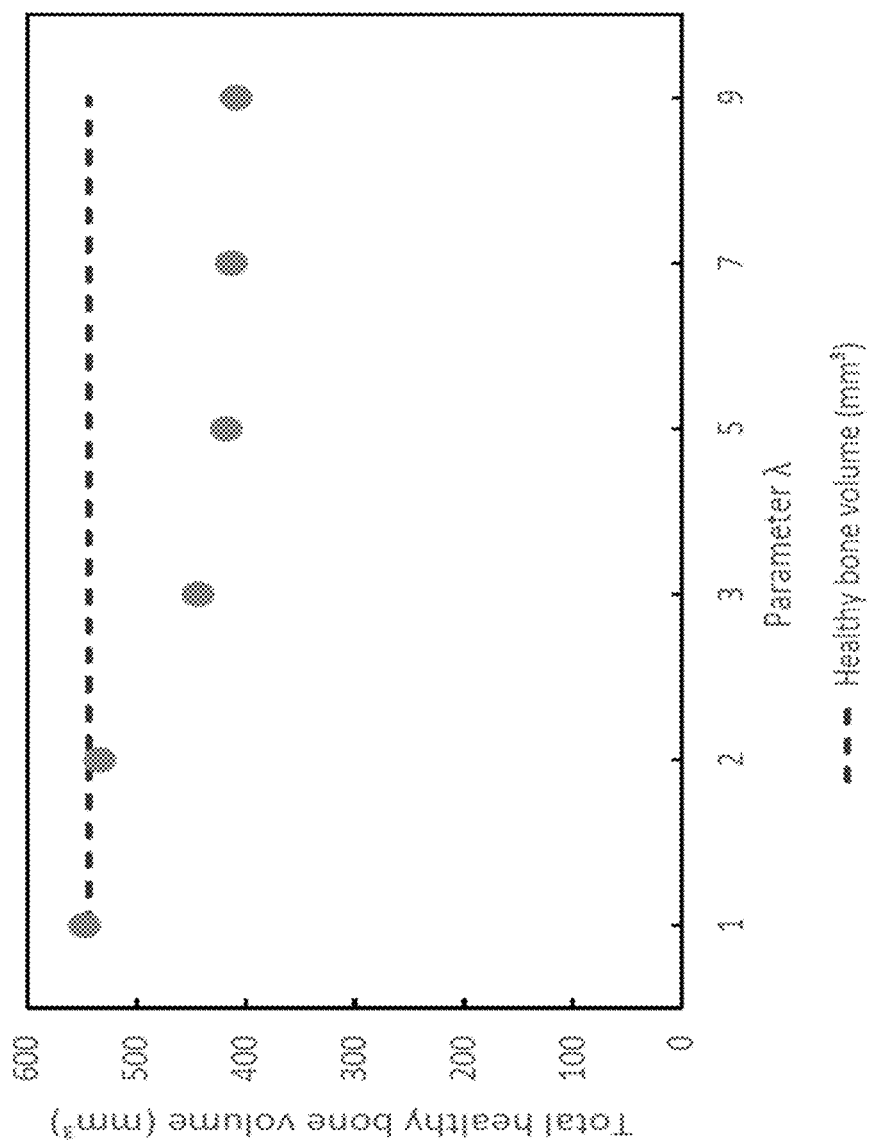
FIG. 11 illustrates the effects of parameter λ on the measured erosion volume.

In reference to FIG. 10, the measured bone volume tends to zero as $\beta$ increases with ideal parameter values being 7 or greater. In reference to FIG. 11, the predicted healthy bone volume tends the original bone volume (no erosion) as $\lambda$ decreases with values less than 2 being ideal in this scenario. FIG. 11 illustrates the effects of parameter $\lambda$ on the measured erosion volume. The parameter should help the transformation predict a healthy surface with the same volume as the original bone surface. A predicted bone volume close to the value of the original bone volume is desirable. Therefore, the chosen parameters of $\beta=11$ and $\lambda=2$ are acceptable values for this application. However, further sensitivity tests on multiple bone sizes, multiple deformities and degrees of disease degradation are required to increase accuracy. It must also be noted that the outcome measures reported here are dependent on the chosen parameters or the CPD code.

Figures 12A, 12B, 12C:
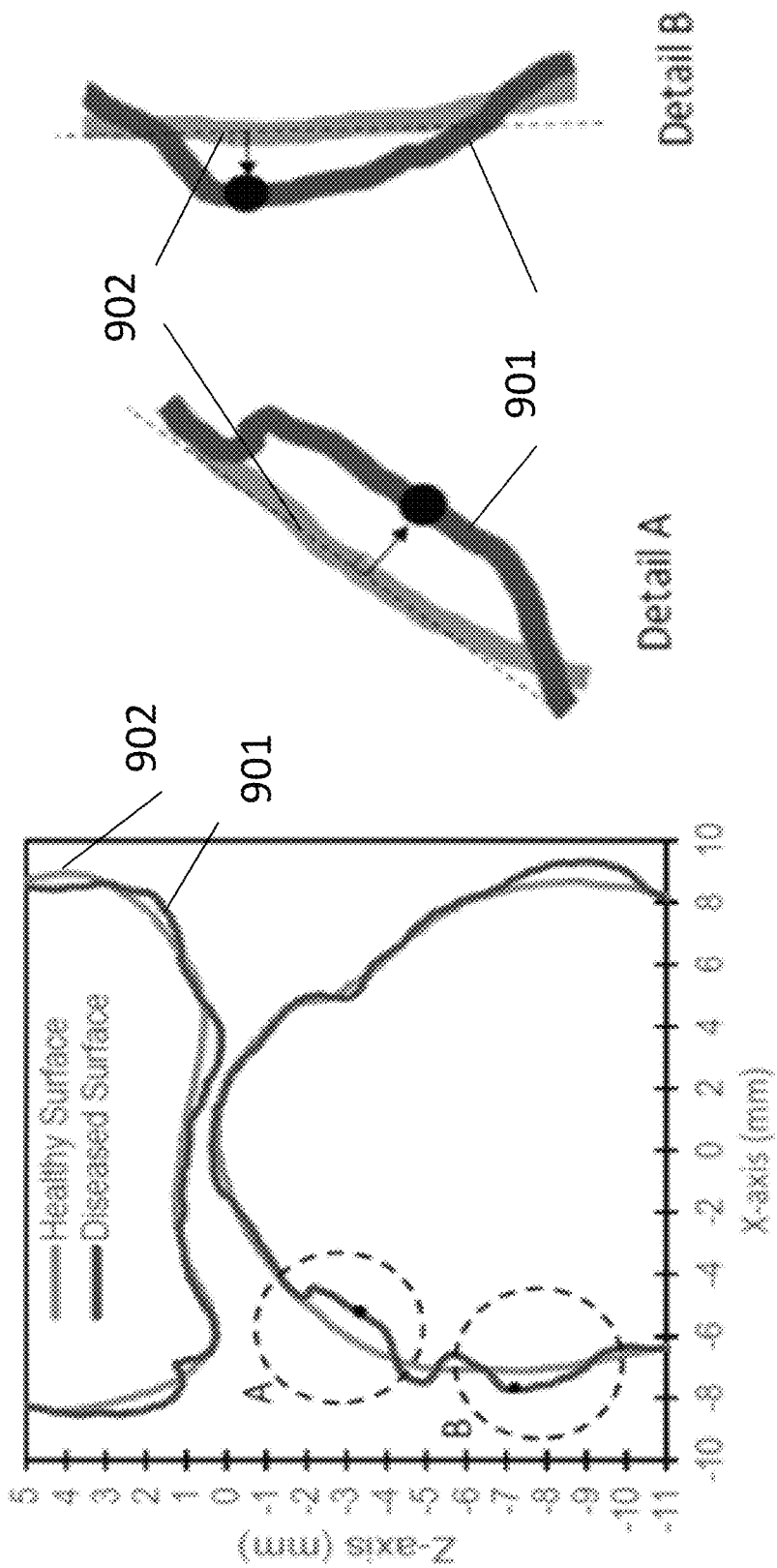
FIGS. 12A-12C illustrate a cross-sectional profile of metacarpophalangeal joint with diseased surface overlaid the corresponding predicted healthy surface.

In some embodiments, to quantifying surface deformity, surface deformity can be characterized as the deviation of the patient bone surface from the corresponding predicted healthy surface. For example, FIG. 12A illustrates a cross-sectional profile of metacarpophalangeal joint with diseased surface (901) overlaid the corresponding predicted healthy surface (902). A negative distance represents bone erosion (FIG. 12B), whilst a positive distance represents periosteal bone growth (FIG. 12C). These distances, calculated over the entire 3D surface, can be used to develop outcome measures to describe the degree of bone degradation as a function of surface deviation.

In some embodiments, percentage surface area of periosteal bone growth and erosion can be used. The total bone surface area determined to be "diseased" (i.e., comprised of abnormal erosions or growths) can be represented as a percentage of the total analyzed surface area. A threshold can be selected from the sensitivity analysis, described below, where distances exceeding this threshold can be considered "diseased". This outcome can be further categorized into areas of erosion and periosteal bone growth, each expressed as a percent of the total surface area.

In some embodiments, mean distance between surfaces can be used. The extent of the deviation between the predicted healthy surface and the diseased surface can be represented as an average distance, where a large mean distance indicated a greater occurrence of surface deviation in either the positive or negative direction. A negative distance would indicate more erosions, and vice versa for growths.

In some embodiments, maximum positive distance and maximum negative distance between surfaces can be used. Maximum periosteal bone growth height (positive distance) and erosion depth (negative distance) can be expressed in mm. In some embodiments, average standard deviation of distances between surfaces can be used. It can be assumed bone surface with greater standard deviation between the predicted healthy surface and diseased surface is an indication of greater joint degradation.

Number of independent erosion sites and bone growths can be used. In this context, to measure the distance between the predicted healthy surface and the diseased bone surface, the healthy surface can be defined as a point cloud with 10,000 vertices distributed over the surface and the diseased surface is defined as a triangulated mesh. Each triangulation is characterized by three vertices and a face normal. The algorithm calculates the shortest line connecting a point on the healthy surface and a 3D triangulation on the diseased surface using the direction of the respective face normal. The nearest point on the surface as well as the distance is returned as a measurement. The distance is signed according to face normals to identify on which side of the surface the query point resides. Using the triangulation as the boundary condition for area when searching for a respective face for each point in the face normal direction, restricts the algorithm from calculating non-representative distances.

Figure 13:
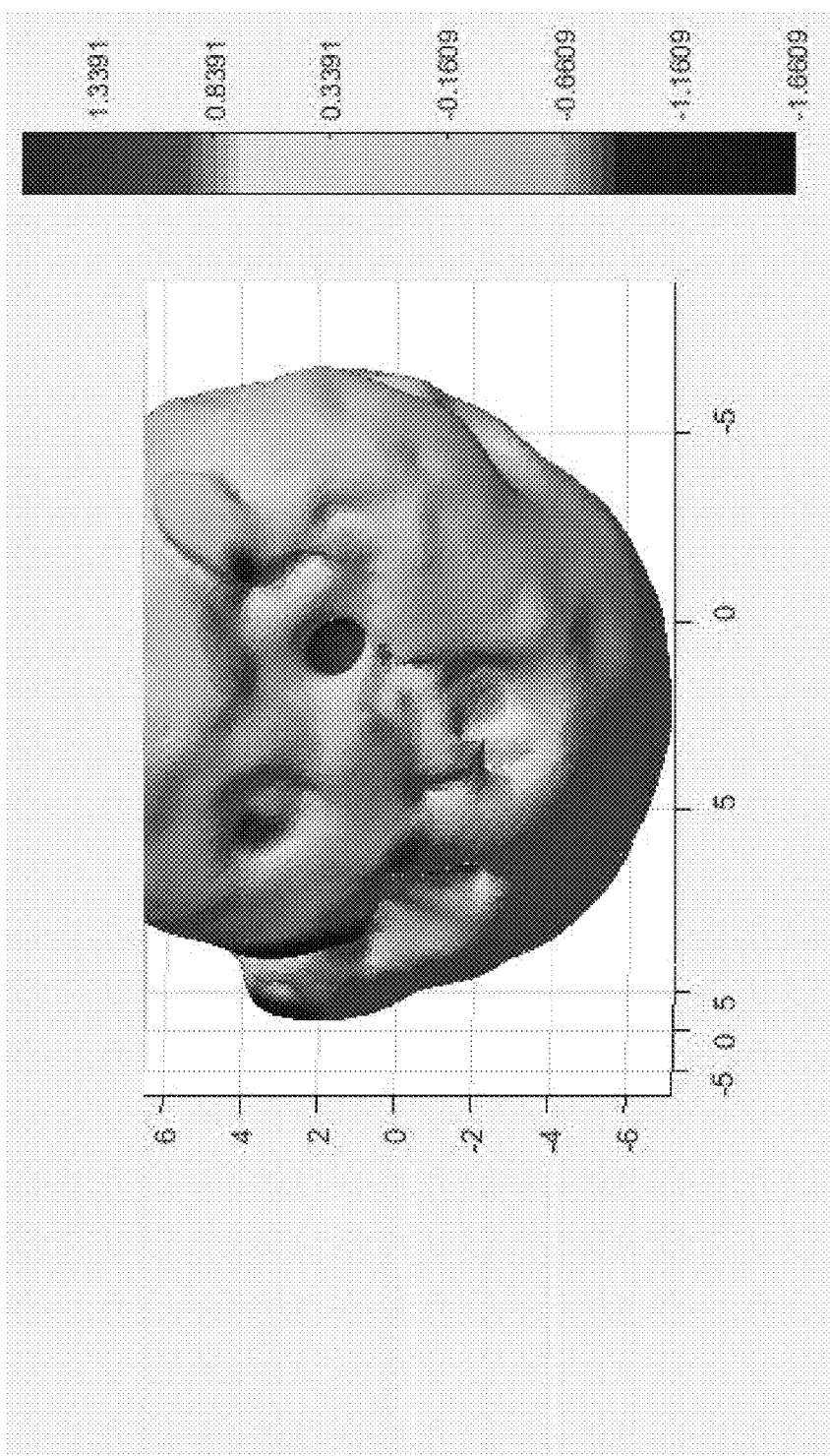
FIG. 13 illustrates a computed 3D image of diseased bone surface with heatmap indicating areas of bone surface degradation.

In reference to FIG. 13, in some embodiments, the instant method generates a 3D image of the diseased surface with an overlaid heat map indicating areas of erosion or periosteal bone growth, To determine the degree to which the calculated parameters depend upon the specific reference surfaces used to produce the generic healthy surface, a sensitivity analysis can be conducted using various healthy surface combinations. To accomplish this, for example, the maximum periosteal bone growth height for three randomly selected diseased surfaces using the various reference surfaces with different combinations of healthy bone surfaces. The percent mean difference of the outcome can be calculated for each reference surface group. Mean and SD can be calculated for each diseased surface. The reference surface groups are made of various combinations of healthy surfaces as listed below.

In some embodiments, randomized surfaces can be used. To determine the extent to which the specific healthy surfaces included within the generic surface mattered, different combinations of healthy surfaces can be selected to create different generic surfaces. The healthy surfaces can be chosen from a pool of healthy surfaces by a random number generator implemented in, for example, MATLAB 2015a (The MathWorks, Inc., Natick, Mass., US). In some embodiments, larger number of surfaces can be used. To determined how many healthy surfaces are required to create a reliable generic healthy reference surface, the number of healthy surfaces used to create the generic surface can be increased. In some embodiments, gender specific surfaces can be used.

To quantify the accuracy and limitations of the algorithm, a series of artificial erosions and periosteal bone growths with known dimensions can be manufactured on different healthy surfaces. Algorithm-based measures, maximum erosion depth, maximum growth height, number of individual erosions and number of individual growths can be compared to the actual known values. The deformities can be constructed by manual manipulation of the already segmented HR-pQCT image masks. Dimensions and shapes can be selected based on clinical reports. For example, erosions can range from 1.9 to 4.9 mm in depth, and periosteal growths can range from 0.6 to 1.9 mm in height. All types of artificial erosions and growths can be placed individually and in combination on the healthy surfaces.

For the validation protocol the following assessments can be made: (1) the ability to detect an erosion or growth, by systematically varying the cut-off threshold. This is the minimum distance between surfaces to be considered an erosion or growth and was determined from the average Youden's Index of the sensitivity and specificity plots. (2) The accuracy of erosion depth calculations. This can be calculated as the root mean squared error (RMSE) of the measured versus actual depth or height. (3) The overall fit of the predicted healthy surface onto a given specific surface. Overall fit can be expressed as the mean distance between the predicted and actual surface, in those regions without artificial erosions and growths.

The methods and systems of the present disclosure are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their disclosure or are they intended to represent that the experiments below are all or the only experiments performed. Efforts have been made to ensure accuracy with respect to numbers used (e.g. amounts, temperature, etc.) but some experimental errors and deviations should be accounted for.

EXAMPLES

Example 1

Methods: In Vivo Images of the Second Metacarpophalangeal (MCP) Joint, including the metacarpal head and phalangeal base, were acquired in cohorts of healthy subjects, subjects with RA and subjects with PsA using HR-pQCT (XtremeCT, Scanco Medical AG, Brüttisellen, Switzerland). Images were acquired on the predominantly affected hand of 17 RA patients (age 61±18 years, 12 females, 5 males) and 17 PsA subjects (age 60±18 years, 7 females, 10 males) and enrolled from the Rheumatology Division at University of Massachusetts Memorial Medical Center (UMMMC). Each patient had radiographic confirmation of erosions and periosteal bone formation on the imaged hand. The healthy cohort consisted of 12 subjects (age 52±14 years, 7 females, 5 males), devoid of known immuno-deficiencies. Each image set consisted of 330 slices with 82 µm isotropic voxel size, encompassing a length of approximately 27 mm spanning the second MCP joint.

Results:

Sensitivity Analysis: The surface matching algorithm was not very sensitive to either the number of surfaces used to create the generic healthy surface, nor the specific healthy surfaces used. When the number of surfaces used to create the generic healthy surface was increased from 2 to 12, calculated maximum periosteal growth for the diseased surfaces that were tested varied by up to 129 µm. Similarly, when different combinations of healthy surfaces were used to create the generic healthy surface, calculated maximum periosteal growth varied by up to 260 µm.

Figure 14:
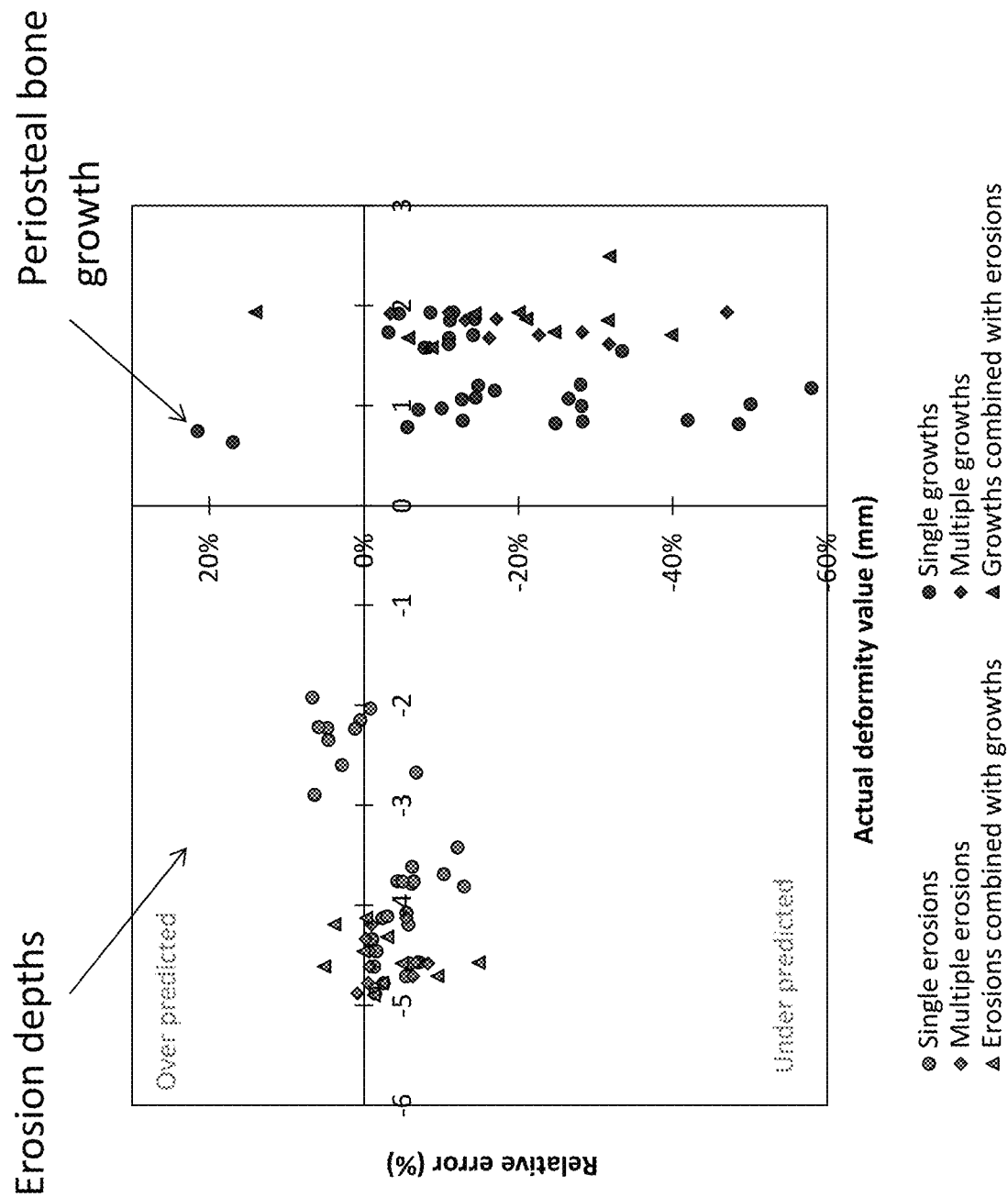
FIG. 14 is a graph showing the relative error between the predicted values and the actual values of the deformity measurements represented as a percentage of the size of the deformity.

Validation: A cut-off threshold of 0.6 mm was able to detect both erosions and periosteal growths with 87.5% sensitivity and 86.8% specificity. This was used for all subsequent calculations. Overall, the algorithm predicted erosion depth more accurately than periosteal bone growth height. For example, FIG. 14 is a graph showing the relative error between the predicted values and the actual values of the deformity measurements represented as a percentage of the size of the deformity. Relative error=(predicted value−actual value)/actual value %. Erosion depth RMSE was 4±3% of the actual value, corresponding to an average precision error of 50 µm. The heights of periosteal bone growths were predicted to within 20±13%, corresponding to an average precision error of 210 The majority of deformity predictions were under-predicted, 72% of erosion depths and 94% of growth heights. The algorithm was best at measuring deep, narrow erosions, and worst at measuring wide, gradual periosteal growths. Overall fit between surfaces was excellent, with an average distance of 0.08 mm.

Application to Patient Cohort: The algorithm objectively illustrated areas of abnormal bone degradation and growth, accompanied by corresponding output data from which bone surface topology could be further analysed. For example, FIG. 15A and FIG. 15B illustrate the visual outputs of the algorithm showing areas of erosion and periosteal bone growth. The heat map represents the distance between the subject bone surface and the corresponding predicted healthy surface. Two examples of diseased surfaces are illustrated in (FIG. 15A) and two examples of healthy surfaces in (FIG. 15B). The prevalence of erosion and bone growth is noticeably observable. The dashed ellipse in the top right panel illustrates a large ridge of abnormal periosteal growth. In the metacarpal head, patients with PsA and RA had maximum positive distances (periosteal bone growth) that were 55% and 57% greater than in the healthy cohort. Similarly, PsA and RA patients had maximum negative distances (erosions) for both the metacarpal head and phalangeal base that were over 85% greater than the healthy cohort as shown in Table 1 below.

Table 1 presents results comparing mean outcome measures of healthy subject surfaces to PsA diseased subject surfaces and RA diseased subject surfaces. Differences between PsA and RA surfaces are included. The outcome measures are reported as mean values±standard deviation.

| Outcome Measure | Metacarpal Results | | | Phalangeal Base Results | | |
|---|---|---|---|---|---|---|
| | Healthy surface | PsA Diseased Surface | RA Diseased Surface | Healthy surface | PsA Diseased surface | RA Diseased Surface |
| Mean distance between surfaces (mm) | −0.07 ± 0.04 | −0.05 ± 0.07 | −0.02 ± 0.06 | −0.04 ± 0.03 | −0.04 ± 0.04[b] | −0.01 ± 0.02[a,b] |
| Maximum positive distance between surfaces (mm) | 0.60 ± 0.13 | 0.93 ± 0.45 | 0.94 ± 0.51 | 0.66 ± 0.05 | 0.87 ± 0.53 | 0.84 ± 0.36 |
| Maximum Negative distance between surfaces (mm) | −0.71 ± 0.28 | −1.31 ± 0.65 | −1.62 ± 1.11[a] | −0.65 ± 0.05 | −1.34 ± 0.68[a] | −1.44 ± 0.82[a] |
| Average Standard deviation of distances between surfaces (mm) | 0.22 ± 0.05 | −0.32 ± 0.17 | 0.28 ± 0.19 | 0.26 ± 0.03 | 0.30 ± 0.20 | 0.21 ± 0.10 |
| Percentage surface area of periosteal bone growth (%) | 0.1% ± 0.2% | 3.8% ± 6.4% | 1.5% ± 2.4% | 0.4% ± 0.5% | 3.0% ± 5.3% | 1.2% ± 2.8% |
| Percentage surface area of erosions (%) | 0.6% ± 1.2% | 6.7% ± 8.7%[a] | 2.8% ± 3.4% | 0.2% ± 0.3% | 4.9% ± 7.2%[a] | 1.7% ± 3.2% |
| Number of independent erosion sites | 0.8 ± 1.1 | 2.9 ± 2.7[a] | 3.5 ± 3.9[a] | 1.1 ± 0.8 | 1.9 ± 2.2[a] | 1.9 ± 3.0 |
| Number of independent bone growths | 0.9 ± 1.0 | 4.5 ± 3.5 | 4.5 ± 4.4 | 0.7 ± 0.7 | 4.0 ± 3.5 | 2.4 ± 2.0 |

[a]Significant difference ($p < 0.05$) for outcome measures between healthy and diseased surfaces.
[b]Significant difference ($p < 0.05$) for outcome measures between PsA and RA diseased subject surfaces Patients with PsA had significantly greater percentages of the metacarpal head and phalangeal base surface area that were eroded compared to the healthy cohort (Table 1).

The algorithm detected significantly more erosion sites on the metacarpal head in both PsA and RA patients, compared to the healthy cohort. Finally the maximum depth of erosions was significantly greater in both the metacarpal head and phalangeal base of RA subjects, and the phalangeal base of the PsA subjects.

The outcome variables were able to discriminate healthy versus RA patients better than healthy versus PsA patients. At the metacarpal head, erosion depth and average surface matching successfully discriminated 96.6% of healthy and RA patient surfaces from each other (11/12 healthy and 17/17 RA surfaces). At the phalangeal base, a combination of erosion depth, periosteal growth height, percent surface eroded and surface variability correctly classified 100% of healthy and RA patient surfaces. At the metacarpal head of healthy and PsA patients, the number of erosion sites and average surface matching discriminated 86.2% correctly (12/12 healthy and 13/17 PsA surfaces). However, at the phalangeal base, erosion depth alone was selected, which discriminated 72.4% of surfaces correctly (12/12 healthy and 9/17 PsA surfaces).

FIG. 16 shows, by way of example, a diagram of a typical processing architecture, which may be used in connection with the methods and systems of the present disclosure. A computer processing device 200 can be coupled to display 212 for graphical output. Processor 202 can be a computer processor 204 capable of executing software. Typical examples can be computer processors (such as Intel® or AMD® processors), ASICs, microprocessors, and the like. Processor 204 can be coupled to memory 206, which can be typically a volatile RAM memory for storing instructions and data while processor 204 executes. Processor 204 may also be coupled to storage device 208, which can be a non-volatile storage medium, such as a hard drive, FLASH drive, tape drive, DVDROM, or similar device. Although not shown, computer processing device 200 typically includes various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 200. Processor 204 may also be coupled to other type of computer-readable media, including, but are not limited to, an electronic, optical, magnetic, or other storage or transmission device capable of providing a processor, such as the processor 204, with computer-readable instructions. Various other forms of computer-readable media can transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Program 210 can be a computer program or computer readable code containing instructions and/or data, and can be stored on storage device 208. The instructions may comprise code from any computer-programming language, including, for example, C, C++, C#, Visual Basic, Java, Python, Perl, and JavaScript. In a typical scenario, processor 204 may load some or all of the instructions and/or data of program 210 into memory 206 for execution. Program 210 can be any computer program or process including, but not limited to web browser 166, browser application 164, address registration process 156, application 142, or any other computer application or process. Program 210 may include various instructions and subroutines, which, when loaded into memory 206 and executed by processor 204 cause processor 204 to perform various operations, some or all of which may effectuate the methods for managing medical care disclosed herein. Program 210 may be stored on any type of non-transitory computer readable medium, such as, without limitation, hard drive, removable drive, CD, DVD or any other type of computer-readable media.

Certain aspects of the present disclosure include process steps and instructions described herein in the form of an algorithm. It should be noted that the process steps and instructions of the present disclosure could be embodied in software, firmware or hardware, and when embodied in software, could be downloaded to reside on and be operated from different platforms used by a variety of operating systems. The disclosure can also be in a computer program product which can be executed on a computing system.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a tangible computer-readable (or machine-readable) storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. In some embodiments, the computer is connected to a display to display the images generated by the instant methods.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description. In addition, the present disclosure is not described with reference to any particular programming language. It will be appreciated that a variety of programming languages may be used to implement the teachings of the present disclosure as described herein, and any references to specific languages are provided for disclosure of enablement and best mode of the present disclosure.

As will be understood by those familiar with the art, the invention may be embodied in other specific forms without departing from the spirit or essential characteristics thereof. Likewise, the particular naming and division of the modules, features, attributes, methodologies, managers and other aspects are not mandatory or significant, and the mechanisms that implement the invention or its features may have different names, divisions and/or formats. Furthermore, as will be apparent to one of ordinary skill in the relevant art, the modules, features, attributes, methodologies, managers and other aspects of the invention can be implemented as software, hardware, firmware or any combination of the three. Of course, wherever a component of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of skill in the art of computer programming. Additionally, the present invention is in no way limited to implementation in any specific programming language, or for any specific operating system or environment.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A method for determining a deformity in a bone surface, the method comprising:
    performing a scan of a healthy bone and a diseased bone;
    creating 3-dimensional (3D) representations of a current surface of the diseased bone;
    constructing an estimated healthy surface in 3D for the diseased bone based on the surface of the healthy bone; and
    identifying a deformity in the diseased bone by comparing the estimated healthy surface to the current surface of the diseased bone.

2. The method of claim 1 wherein the scan is performed using high resolution peripheral quantitative computed tomography (HR-pQCT).

3. The method of claim 1 wherein the 3D representation of the current surface of the healthy bone comprises a composite image of multiple healthy surfaces.

4. The method of claim 3 wherein the composite image of multiple healthy bones is generated by averaging corresponding points on the healthy surfaces.

5. The method of claim 1 further comprising non-rigidly transforming an estimated healthy surface to the current surface of the diseased bone.

6. The method of claim 1 wherein the step of performing comprises performing a scan of respective phalangeal base and metacarpal head.

7. The method of claim 1 wherein the diseased bone is deformed due to rheumatoid arthritis (RA) or psoriatic arthritis (PsA).

8. The method of claim 1 wherein the deformity is identified by identifying deviations between the estimated healthy surface and the current surface.

9. The method of claim 8 wherein the deformity comprises periosteal bone growth or erosions.

10. The method of claim 9 further comprising displaying a comparison of the estimated healthy surface and the current surface of the diseased bone to identify the t deformity.

11. A system for determining a deformity in a bone surface, the system comprising:
an imaging modality;
a controller in communication with the imaging modality, the controller being programmed to receive a scan of a healthy bone and a diseased bone; create 3-dimensional (3D) representations of a current surface of the diseased bone; construct an estimated healthy surface in 3D for the diseased bone based on the surface of the healthy bone;
and identify a deformity in the diseased bone by comparing the estimated healthy surface to the current surface of the diseased bone.

12. A method for determining a deformity in a bone surface, the method comprising:
performing HR-pQCT scans of healthy bone surfaces in healthy cohort and of a diseased bone surface of a patient in a deceased cohort;
preparing 3D images of surfaces of the healthy bone surfaces and diseased bone surface;
scaling and aligning the 3D images;
applying anatomical markers to the 3D images of the healthy bone surfaces;
creating a 3D image of an estimated healthy surface from the 3D images of the healthy bone surfaces;
non-linearly transforming the 3D image of the estimated healthy surface to the 3D image of the diseased bone surface; and
displaying a comparison of the estimated healthy surface and the diseased bone surface of to identify a deformity in the diseased bone surface.

13. The method system of claim 11 wherein the controller is further programmed to non-rigidly transform an estimated healthy surface to the current surface of the diseased bone.

14. The system of claim 13 wherein the scan is performed using high resolution peripheral quantitative computed tomography (HR-pQCT).

15. The system of claim 13 wherein the 3D representation of the current surface of the healthy bone comprises a composite image of multiple healthy surfaces.

16. The system of claim 15 wherein the composite image of multiple healthy bones is generated by averaging corresponding points on the healthy surfaces.

17. The system of claim 13 wherein the diseased bone is deformed due to rheumatoid arthritis (RA) or psoriatic arthritis (PsA).

18. The system of claim 13 wherein the deformity is identified by identifying deviations between the estimated healthy surface and the current surface.

19. The system of claim 18 wherein the deformity comprises periosteal bone growth or erosions.

20. The system of claim 13 further comprising a display for displaying a comparison of the estimated healthy surface and the current surface of the diseased bone to identify the deformity.

* * * * *

UNITED STATES PATENT AND TRADEMARK OFFICE
CERTIFICATE OF CORRECTION

PATENT NO. : 10,603,005 B2
APPLICATION NO. : 15/924946
DATED : March 31, 2020
INVENTOR(S) : Henchie et al.

Page 1 of 1

It is certified that error appears in the above-identified patent and that said Letters Patent is hereby corrected as shown below:

In the Claims

Claim 10, Column 15, Line 3, the text "t deformity" should only read -- deformity --

Claim 12, Column 16, Line 5, the text "surface of to identify" should read -- surface to identify --

Claim 13, Column 16, Line 7, the text "The method system of" should read -- The system of --

Claims 14, 15, 17, 18 and 20, the text "The system of claim 13" should all read -- The system of claim 11 --

Signed and Sealed this
Twenty-first Day of July, 2020

Andrei Iancu
*Director of the United States Patent and Trademark Office*